US007060289B2

(12) United States Patent
Wassenaar

(10) Patent No.: US 7,060,289 B2
(45) Date of Patent: Jun. 13, 2006

(54) TOPICAL GLYCOPYRROLATE PRODUCT

(75) Inventor: Willem Wassenaar, Toronto (CA)

(73) Assignee: PurePharm Inc., Toronto (CA)

( * ) Notice: Subject to any disclaimer, the term of this patent is extended or adjusted under 35 U.S.C. 154(b) by 0 days.

(21) Appl. No.: 10/140,154

(22) Filed: May 8, 2002

(65) Prior Publication Data
US 2003/0211134 A1 Nov. 13, 2003

(30) Foreign Application Priority Data
May 3, 2002 (CA) .................................. 2384922

(51) Int. Cl.
- A61K 9/70 (2006.01)
- A61K 9/00 (2006.01)
- A61K 9/08 (2006.01)
- A61K 31/40 (2006.01)

(52) U.S. Cl. .................. 424/443; 424/400; 424/401; 424/402; 514/424

(58) Field of Classification Search .............. 424/400, 424/402, 401, 443, 403; 514/424
See application file for complete search history.

(56) References Cited

U.S. PATENT DOCUMENTS 5,996,797 A * 12/1999 Flaig .......................... 206/494
6,433,003 B1 * 8/2002 Bobrove et al. ............ 514/424
6,446,795 B1 * 9/2002 Allen et al. ................. 206/210

FOREIGN PATENT DOCUMENTS

WO     WO 99/6793     * 12/1999

* cited by examiner

Primary Examiner—Michael Hartley
Assistant Examiner—Simon J. Oh
(74) Attorney, Agent, or Firm—Clark & Brody

(57) ABSTRACT

This invention relates to a convenient and safe product and method of applying glycopyrrolate topically in order to reduce excessive sweating in localized areas for those who suffer from this condition. This invention also relates to combining oral and topical delivery of glycopyrrolate to reduce excessive sweating and minimize side effects. This invention also relates to a convenient and safe product and method of applying glycopyrrolate topically to areas of compensatory sweating after endoscopic thoracic sympathectomy.

1 Claim, No Drawings

TOPICAL GLYCOPYRROLATE PRODUCT

FIELD OF THE INVENTION

This invention relates to a convenient and safe product and method of applying glycopyrrolate topically in order to reduce excessive sweating in localized areas for those who suffer from this condition. This invention also relates to combining oral and topical delivery of glycopyrrolate to reduce excessive sweating and minimize side effects. This invention also relates to a convenient and safe product and method of applying glycopyrrolate topically to areas of compensatory sweating after endoscopic thoracic sympathectomy.

For most people sweating is a normal response to heat stress and is important in maintaining body temperature. However, in some individuals sweating can be excessive and unrelated to heat stress. This excessive sweating can be embarrassing and can severely limit social activities. The areas typically involved in excessive perspiration are 1) face including the neck and scalp 2) armpits 3) hands 4) back of the knees 5) feet 6) groin, and 7) in the case of compensatory sweating, the trunk.

Nerve impulses from the brain stimulate sweat glands and cause perspiration. Sometimes the nerves stimulate excessive sweating unrelated to the normal process of temperature control.

The use of topical glycopyrrolate has been reported over the past 20 years. Here is a table of clinical papers reporting use of glycopyrrolate and the topical formulation used.

Treatment of Hyperhidrosis and Gustatory Sweating

| Author | Year | Concentration | Formulation | Notes |
|---|---|---|---|---|
| Hay | 1978 | 0.5 & 1.0% | Solution and cream presentations | Cotton applicator used to apply solution. |
| Hay | 1982 | 0.5, 1 & 2% | Roll-on solution, distilled water used. | Glycopyrrolate crystalized out when concentrations above 2%. pH adjusted to 2.5 to 4.0 Few patients need to rub lotion into the skin to get better effects. |
| Hay | 1982 | 2 & 4% | HEB cream base (Barnes- Hind | Solution worked better than cream. |
| May | 1989 | 0.5, & 2.0% | 0.5 & 2.0% roll-on; 2.0% cream. Used Hays formulation. | almost all patients obtained total or partial relief. Placebo treatment yielded no response. |
| Atkin | 1996 | 0.50% | cetamacrogol A formulation cream base | Crushed Robinul ™ tablets mixed into cream |
| Shaw | 1997 | 0.50% | cetamacrogol A formulation cream base | |
| Seukeran | 1998 | 2% | cetamacrogol A formulation cream base | Could not get cream into hairline. Cream and sweat mixture unacceptable. |
| Seukeran | 1998 | 0.50% | aqueous solution | Worked well |
| Urman | 1999 | 0.50% | Lotion in a roll-on dispenser | |

BACKGROUND OF THE INVENTION

Hays first reported on the topical application of glycopyrrolate for facial sweating associated with eating (gustatory sweating). (1, 2) Subsequently others have reported on the use of topical glycopyrrolate for hyperhidrosis and gustatory sweating. Oral glycopyrrolate has also been used for hyperhidrosis. Glycopyrrolate does not cure any underlying causes of hyperhidrosis or gustatory sweating, but reduces or prevents the resulting excessive sweating.

Use of glycopyrrolate as an anti-secretagogue in the treatment of peptic ulcer disease commenced in Canada in 1961. It continues to be used as an antisialogogue in patients with drooling and as a premedication for anaesthesia to prevent excessive secretions.

Glycopyrrolate is a quaternary amine, which acts as an antimuscarinic, anticholinergic agent. It does not cross the blood brain barrier and it penetrates biological membranes slowly and therefore, when given topically leads to very few side effects.

As with all members of this class, glycopyrrolate should not be used by people with glaucoma or cardiac arrhythmias. Glycopyrrolate should also not be used by people with bladder obstruction, a rapid heart rate, an allergy to glycopyrrolate, or when pregnant or breast-feeding.

Here are the details from one of these papers. In a recent clinical trial (Shaw, J. E., C. A. Abbott, et al. (1997)) to determine if topical glycopyrrolate is able to control diabetic gustatory sweating, the authors found that topical glycopyrrolate is an acceptable safe and effective treatment for diabetic gustatory sweating. A placebo or glycopyrrolate 0.5% cream was self administered by hand to the face and neck. A challenge test was administered, at baseline and at the end of each of the treatment periods. The sweat challenge test measures the amount of sweat produced on the forehead relative to reference sites on the arm and the leg. Glycopyrrolate treated patients had a statistically significant reduction in sweat production during the challenge test (p=0.008). Daily diary records indicated that topical glycopyrrolate treatment resulted in a reduction in frequency and severity of gustatory sweating compared to the placebo treatment (p=0.004). One patient out of 14 discontinued therapy because of a local skin reaction. No other adverse effects were reported.

SUMMARY OF THE INVENTION

This invention relates to a pad containing an amount of glycopyrrolate in solution, for topical application of a therapeutically effective amount of glycopyrrolate, which is useful in reducing sweating in humans. In an embodiment of this invention, the solution is a 5 to 66% ethanol solution and the amount of glycopyrrolate in solution is greater than 0.25% and not more than 6%, particularly 1%, 2% or 3% glycopyrrolate, or greater than 2.5 milligrams and not more than 60 milligrams of glycopyrrolate.

In an embodiment of the invention the pad is a 75:25 rayon and polypropylene pad containing about 1 ml of an about 2% glycopyrrolate/32% ethanol solution for topical application, which is useful in reducing sweating in humans.

This invention also relates to a container containing multiple pads of glycopyrrolate comprising a lid that is capable of being easily opened and closed and functions to prevent evaporation when closed.

This invention also relates to a use of a pad containing an amount of glycopyrrolate in solution, for topical application of a therapeutically effective amount of glycopyrrolate to any part of the human body on which the reduction of sweating is desired, with the exception of mucous membranes.

This invention also relates to a use of a pad containing an amount of glycopyrrolate in solution, for topical application of a therapeutically effective amount of glycopyrrolate to any part of the human body on which the reduction of sweating is desired (with the exception of mucous membranes) in combination with another oral and/or topical therapy for reduction of sweating.

This invention also relates to a method of preparing a container of pads containing a 2% glycopyrrolate solution comprising:
  Mixing 66.7 mL distilled water and 33.3 mL 95% ethanol together to form an ethanol solution;
  Adding 2 grams of glycopyrrolate powder to said ethanol solution and stirring until completely dissolved;
  Adjusting the pH level of said glycopyrrolate solution to 4.0 with hydrochloric acid;
  Pouring 30 to 36 mL of said glycopyrrolate solution onto the top pad of a container of 30 rayon/polypropylene pads; and
  Covering the container with a resealable lid.

DESCRIPTION

Introduction

Excessive sweating can cause embarrassment in social situations and an effective treatment is desirable. Glycopyrrolate has been used orally and topically in the past to reduce excessive sweating. As indicated above, glycopyrrolate has been formulated for topical use as a cream, solution and roll-on, and has been applied using a cotton swab as an applicator.

Using the previously available delivery methods, the topical application of glycopyrrolate can be messy and inconvenient. Oral treatment is simple to administer, however, oral treatment has systemic effects and this causes increased side effects.

Accordingly, the inventors developed a new topical delivery product and method for glycopyrrolate, namely glycopyrrolate on pads. As well, the inventors combined the use of topical glycopyrrolate with oral glycopyrrolate to achieve maximum sweat control and minimal side effects.

Use of Invention

The topical application of glycopyrrolate is especially convenient for those patients who have localized sweating of the face and hands. This invention provides a convenient and safe method to apply glycopyrrolate to the skin in order to reduce excessive sweating in localized areas in those who suffer from this condition. The present invention of glycopyrrolate pads has benefits over previously used topical glycopyrrolate as follows:
  1. Ease of application;
  2. Coverage of large flat surface such as face and neck (roll-on applies narrow band);
  3. Rubbing or massaging formulation into skin for better efficacy (Hays 1982 showed this gave better efficacy in some patients);
  4. Applying approximately the same amount of medication at each use;
  5. A formulation that will allow application into the hairline at the margins of the face since in gustatory sweating, facial sweating extends into the hairline;
  6. A rapidly drying non-greasy, residue free formulation that permits the applications of cosmetics over top;
  7. A hypoallergenic formulation containing no known allergens, unless a preservation agent (antibacterial or chemical stabilizer) is added, as may be required for commercial formulations; and
  8. A formulation that can be prepared in a wide range of strengths to accommodate the variability of glycopyrrolate absorption between different individuals; (Hays 1982, Rautakorpi 1998, provide evidence in their clinical paper on variable absorption)
  9. Convenient to use on the spot before certain events, for example to reduce sweating on the palms to enhance performance in situations such as golf or baseball etc, and to reduce sweating in situations such as business presentations and performing arts.

A surgical procedure called endoscopic thoracic sympathectomy (ETS), the cutting or clipping of fibers of the sympathetic nervous system, is also used to treat the condition of excessive sweating. One of the side effects of this procedure is compensatory sweating in adjacent areas not affected by the surgical procedure. The present invention provides a convenient and safe method of applying glycopyrrolate topically for those patients with areas of compensatory sweating after endoscopic thoracic sympathectomy.

For those with excessive sweating over a very large body surface area and severe sweating in localized areas such as the hands, feet and face, a combination of oral and topical delivery of glycopyrrolate provides the best balance of sweat control and minimizing side effects. This invention also relates to combining oral and topical delivery of glycopyrrolate to reduce excessive sweating and minimize side effects.

Oral glycopyrrolate reduces excessive sweating, but in some patients localized problem areas e.g. hands or feet still remain. To get complete control the patient may not wish to increase the oral dose because then the side effects become intolerable. Topical glycopyrrolate applied locally to the problem spots improves the over all control of hyperhidrosis. Because of its local application, it does not result in additional side effects. Use of the invention can also be combined with other forms of topical glycopyrrolate, such as, glycopyrrolate in gel or cream form or a metered spray of a solution of glycopyrrolate.

Some patients have excessive sweating of the hands and trunk. (There are other combinations such as face, hands and trunk or hands and feet etc.) The hands, face, feet and axilla are usually worse than the trunk. Topical application works well for the local areas (hands, face, feet, axilla). But, areas such as the back may not be as accessible for self-application. If the surface area is too difficult or too large to cover with the topical product, the addition of an oral preparation helps to treat hyperhidrosis more effectively than topical alone.

Finally, the topical glycopyrrolate invention may be used as an antiperspirant for individuals who experience ordinary sweating. Such use may be over the body, but it is particularly effective on the underarms. Sweating is a normal body response and use on only the underarms is recommended for those who experience ordinary sweating. In this way, the body's normal sweat production is not impeded anywhere but the underarm and potential side effects are minimized.

The topical glycopyrrolate invention may incorporate perfumes, scents, preservation agents, moisturizers and the like, as are found in underarm deodorants, provided that such additives do not compromise the effectiveness of the glycopyrrolate.

Development of Invention

Formulations Examined

In order to provide an improved topical formulation, a water-based formulation was desired. Glycopyrrolate dissolves readily in water. However, alcohol was added to the formulation to improve the speed of drying. Glycopyrrolate also dissolves readily in alcohol. Some tested formulations and results were as follows:

1. A 100% distilled water formulation was too slow in drying when applied to the skin
2. A mixture of 33.3% distilled water and 66.7% of 95% ethanol, evaporated rapidly but caused excessive drying. A bitter tasting residue was left on the skin.
3. A mixture of 66.7% distilled water and 33.3% of 95% ethanol dried faster than 100% distilled water but did not cause the drying associated with the solution containing 66.7% of 95% ethanol.

A solution of 66.7% distilled water and 33.3% of 95% ethanol was chosen to deliver the glycopyrrolate. However, any solution which meets the criteria of dissolving glycopyrrolate, being absorbed by an application pad, and quick drying without causing harm to the skin, can be used.

A concentration of glycopyrrolate greater than 0.1% is desirable since 0.1% has been shown to be ineffective (Hays 1978). A 1% glycopyrrolate solution was initially chosen for testing purposes. However, the range of glycopyrrolate can vary to meet the needs of the patient. The upper limit could be at least as high as 6%, although mild side effects begin to present themselves after 4% (Hays 1978).

Preparation of 100 mL Solution of 1% Glycopyrrolate

A 1% glycopyrrolate solution was made by dissolving glycopyrrolate powder in the 66.7 mL distilled water and 33.3 mL of 95% ethanol solution.

Take water 66.7 mL

Add 95% ethanol 33.3 mL

Adjust pH to 4.0 (range 3.5 to 4.5) with a few drops of hydrochloric acid

Add 1 gram of glycopyrrolate stir until glycopyrrolate completely dissolved.

To make 2% solution add 2 gram glycopyrrolate instead of 1 gram etc.

The resulting solution of glycopyrrolate contains approximately 31.635% of ethanol. To avoid skin irritation, the pH of the formulation should be close to that of the skin (pH 5.5). For the chosen 66.7%/33.3% distilled water/95% ethanol solution, the pH level was adjusted to 4.0 with hydrochloric acid. The pH of 4.0 was chosen for stability of the solution and to be as close to the pH of the skin (pH 5.5) as possible.

Application Pads Tested

The inventors discovered that glycopyrrolate could be delivered effectively using pads. The patient could easily and quickly apply the glycopyrrolate with a pad, which allowed the glycopyrrolate to be massaged into the skin for improved results.

Cotton Cosmetic Pads

Here is the experiment conducted to determine the absorbency of cotton cosmetic pads.

| Solution | Dry weight of pad in grams | Wet weight of pad | Weight of solution absorbed | Calculated amount of glycopyrrolate (assuming a 1% solution |
|---|---|---|---|---|
| Water | 0.53 | 7.98 | 7.4 | 74 mg |

These cotton cosmetic pads absorbed too much liquid making it difficult to control the application of the solution to the skin.

75% Rayon/25% Polypropylene Pads

Here is the experiment to determine the absorbency of rayon/polypropylene pads, using the brand of Kleentest™ #9807 2.125 diameter pads, comprised of 75% rayon and 25% polypropylene by weight.

| Solution | Average dry weight (N = 10) | Average wet weight (N = 10) | Average weight of solution absorbed (N = 10) | Calculated amount of glycopyrrolate (assume 1% solution) |
|---|---|---|---|---|
| Water | 0.196 | 1.393 | 1.197 | 11.9 mg |
| 33.3% 95% Ethanol/66.7% Water | 0.192 | 1.219 | 1.027 | 10.3 mg |
| 66.7% 95% ethanol/33.3% Water | 0.195 | 1.034 | 0.839 | 8.4 mg |

These pads hold about 1 mL of liquid, are easy to apply to skin, and do not drip.

These pads impregnated with 1% glycopyrrolate solution of 66.7%/33.7% distilled water/95% ethanol contain about 10 mg of glycopyrrolate.

Variability in Pad Content Due to Stacking

The effectiveness of the glycopyrrolate solution on a pad also depends on whether the invention can be delivered to the patient for use. Several pads must be packaged in such a way that each individual pad delivers a desirable amount of glycopyrrolate.

The brand of Kleentest™ #9807 2.125 diameter pads are packaged for consumer use in stacks of 30. Tests were conducted to determine which solution would give the best content uniformity in each pad from top of the stack to the bottom of the stack. A 1% solution was desired from the above experiment.

The following experiment was conducted to determine if a consistent amount of glycopyrrolate was delivered per pad. Thirty to thirty-six ml of solution were added to ajar containing a stack of 30 of the brand of Kleentest™#9807 2.125 diameter pads. The average weight of the top six pads was compared to the bottom 6 pads.

| Solution | Water | 33.3% 95% Ethanol/ 66.7% Water | 66.7% 95% Ethanol/ 33.3% Water |
| --- | --- | --- | --- |
| Av Net Wt Top 6 | 1.08 g | 0.95 | 0.84 |
| Av Net Wt Bottom 6 | 1.31 g | 1.11 | 0.9 |
| Difference | 18% | 15% | 7% |

The 66.7% 95% ethanol/33.3% water solution yields the smallest percent variation from the average of the top 6 pads to the average of the bottom 6 pads. Increasing the water content to 66.7 and 100% increases the percent variation from 15% to 18%, respectively.

Preferred Invention of Glycopyrrolate on Pads

Other pads may be used as effectively if they meet the following criteria:
1. Pads made of a material able to hold about 1 mL of solution.
2. Solution containing from 0.25% to 6% glycopyrrolate.
3. Aqueous solution having an ethanol content greater than 5% and less than 66%.
4. May also contain suitable preservatives, anti-fungals, anti-bacterials and perfumes.

Use of Glycopyrrolate Pads

Take one pad and apply to the affected area once daily. If required a second pad may be used for large surface areas.

Directions for using on face, hands, feet or armpits:
1. Remove a single pad from the jar.
2. Wipe affected area as desired.
3. Apply any cosmetics or creams only after the applied liquid has dried.
4. Do not wash the treated area for at least 4 hours.
5. Avoid applying to mouth, eyes or mucous membranes. Contact lens users: Insert contact lens before handling glycopyrrolate pads or wash hands thoroughly before inserting lens.
6. Do not apply to cut or broken skin.
7. Discontinue use if rash or skin irritation develops.
8. Keep product away from children and pets.
9. Close container firmly after use to prevent evaporation. Protect from heat.

EXAMPLES OF PATIENT RESPONSES TO GLYCOPYRROLATE PADS

The following examples show how the invention has worked for individual patients, that is, delivering a therapeutically effective amount of glycopyrrolate to reduce sweating, and how it can be adjusted for any patient. For instance, if a patient is finding that the topical pads of glycopyrrolate of the invention provide acceptable reduction in sweating but experiences side effects such as dry mouth, the strength of the glycopyrrolate in solution can be reduced to provide the best results without side effects. Conversely, if sweating has not been reduced to acceptable levels, the strength of the glycopyrrolate in solution can be increased.

Topically applied glycopyrrolate penetrates the skin over the sweat glands and acts as a shield preventing overstimulation of the sweat glands. The effectiveness of the topical glycopyrrolate invention depends on the amount of nerve stimulation each individual brain produces, the thickness of the skin over the sweat glands and the concentration of glycopyrrolate. Most patients enjoy effective control of sweating using the regular strength of 2% glycopyrrolate, however, personalized strength pads can be prepared to maximize the benefit from the treatment.

Generally topical glycopyrrolate should be made in the range of a 0.25% to 6% solution to deal with individual variability in penetration of biological membranes.

1. A 35 year old, male patient with excessive forehead and groin sweating resulting in a facial rash and fungal infection was advised to try the invention. The patient was started on a 1% pad. After 2 weeks the patient reported that the glycopyrrolate pads had worked so well that they had changed his life. His facial and groin sweating had improved markedly and as a result the chronic fungal infection of his groin and constant facial rash had both improved. He was able to participate in social situations that previously would have made him feel very uncomfortable. The patient experienced no side effects while using the 1% strength glycopyrrolate pads. The patient wished to reduce his residual sweating. The patient is now using used 1.5% strength glycopyrrolate pads and has obtained satisfactory control of his sweating. He has not experienced any side effects.

2. A 50 year old, male patient with excessive facial sweating was searching for an alternative to oral therapy. The patient had been taking up to 6, 15 mg capsules per day of propanthaline, an oral anticholinergic. The patient was started on 1% strength glycopyrrolate pads then moved to 2% strength glycopyrrolate pads and finally 3% strength glycopyrrolate pads. The 3% strength glycopyrrolate pads gave the patient almost complete control of his facial sweating. The patient did not experience any side effects while using 3% strength glycopyrrolate pads. The patient only occasionally uses oral propantheline.

3. A 40 year old male, suffering from excessive facial and scalp sweating began using 1% strength glycopyrrolate pads on his face. He was able to control his facial sweating. At the time of re-ordering the 1% strength glycopyrrolate pads, he asked if there was a more efficient manner for him to apply the medication to the top and back of his scalp. The pad was not allowing him to penetrate his strands of hair to apply the medication directly to his scalp. He was provided with a 1% solution of glycopyrrolate in water and ethanol in a metered spray container. The patient uses the spray to apply the glycopyrrolate solution to his scalp. The 1% glycopyrrolate solution in a metered spray bottle was able to satisfactorily reduce his scalp sweating. The patient also uses 1% strength glycopyrrolate pads to control his facial flushing. The patient has not experienced any side effects with the topical application of glycopyrrolate.

Bibliography

1. Hays, L. L. (1978). "The Frey syndrome: a review and double blind evaluation of the topical use of a new anticholinergic agent." *Laryngoscope* 88(11): 1796–824.
2. Hays, L. L., A. J. Novack, et al. (1982). "The Frey syndrome: a simple, effective treatment." *Otolaryngol Head Neck Surg* 90(4): 419–25.
3. Abell, E. and K. Morgan (1974). "The treatment of idiopathic hyperhidrosis by glycopyrronium bromide and tap water iontophoresis." *Br J Dermatol* 91(1): 87–91.
4. Ali-Melkkila, T., T. Kaila, et al. (1989). "Glycopyrrolate: pharmacokinetics and some pharmacodynamic findings." *Acta Anaesthesiol Scand* 33(6): 513–7.
5. Atkin, S. L. and P. M. Brown (1996). "Treatment of diabetic gustatory sweating with topical glycopyrrolate cream." *Diabet Med* 13(5): 493–4.
6. Berrios, R. J. and P. D. Quinn (1986). "Frey's syndrome: complication after orthognathic surgery." *Int J Adult Orthodon Orthognath Surg* 1(3): 219–24.
7. Bronshvag, M. M. (1978). "Spectrum of gustatory sweating, with especial reference to its presence in diabetics with autonomic neuropathy." *Am J Clin Nutr* 31(2): 307–9.
8. May, J. S. and W. F. McGuirt (1989). "Frey's syndrome: treatment with topical glycopyrrolate." *Head Neck* 11(1): 85–9.
9. Rautakorpi, P., T. Manner, et al. (1998). "Pharmacokinetics and oral bioavailability of glycopyrrolate in children." *Pharmacol Toxicol* 83(3): 132–4.
10. Seukeran, D. C. and A. S. Highet (1998). "The use of topical glycopyrrolate in the treatment of hyperhidrosis." *Clin Exp Dermatol* 23(5): 204–5.
11. Shaw, J. E., C. A. Abbott, et al. (1997). "A randomised controlled trial of topical glycopyrrolate, the first specific treatment for diabetic gustatory sweating." *Diabetologia* 40(3): 299–301.
12. Sheehy, T. W. (1991). "Diabetic gustatory sweating." *Am J Gastroenterol* 86(10): 1514–7.
13. Stern, L. M. (1997). "Preliminary study of glycopyrrolate in the management of drooling." *J Paediatr Child Health* 33(1): 52–4.
14. Stuart, D. D. (1978). "Diabetic gustatory sweating." *Ann Intern Med* 89(2): 223–4.
15. Urman, J. D. and A. M. Bobrove (1999). "Diabetic gustatory sweating successfully treated with topical glycopyrrolate: report of a case and review of the literature." *Arch Intern Med* 159(8): 877–8.

I claim:

1. A method of preparing a container of pads containing a 2% glycopyrrolate solution comprising:
  a. Mixing 66.7 mL distilled water and 33.3 mL 95% ethanol together to form an ethanol solution;
  b. Adding 2 grams of glycopyrrolate powder to said ethanol solution and stirring until completely dissolved;
  c. Adjusting the pH level of said glycopyrrolate solution to 4.0 with hydrochloric acid;
  d. Pouring 30 to 36mL of said glycopyrrolate solution onto the top pad of a container of 30 rayon/polypropylene pads; and
  e. Covering the container with a resealable lid.

* * * * *